United States Patent [19]

Pallos

[11] 4,321,083
[45] Mar. 23, 1982

[54] N-ACYL-PHENYL-THIOUREA HERBICIDAL ANTIDOTES

[75] Inventor: Ferenc M. Pallos, Walnut Creek, Calif.

[73] Assignee: Stauffer Chemical Company, Westport, Conn.

[21] Appl. No.: 142,531

[22] Filed: Apr. 21, 1980

[51] Int. Cl.³ .............................................. A01N 25/32
[52] U.S. Cl. .............................................. 71/99; 71/88; 71/94; 71/100; 564/23
[58] Field of Search .............................. 71/100, 99, 94, 88; 564/23

[56] References Cited

U.S. PATENT DOCUMENTS 2,913,327  11/1959  Tilles ........................................ 71/100
3,185,720   5/1965  Tilles et al. ............................ 260/55 A Primary Examiner—Catherine L. Mills
Attorney, Agent, or Firm—Harry A. Pacini

[57] ABSTRACT

Compounds having the formula

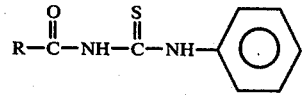

in which R is alkyl having 1-4 carbon atoms and have utility for the protection of crops from herbicidal injury.

4 Claims, No Drawings

N-ACYL-PHENYL-THIOUREA HERBICIDAL ANTIDOTES

BACKGROUND OF THE INVENTION

Uses of Herbicides

A herbicide is a compound which controls or modifies plant growth, e.g., killing, retarding, defoliating, desiccating, regulating, stunting, tillering, stimulating, dwarfing and the like. "Plant" refers to all physical parts, including seeds, seedlings, saplings, roots, tubers, stems, stalks, foliage and fruits. "Plant growth" is meant to include all phases of development from seed germination to natural or induced cessation of life.

Herbicides are generally used to control or eradicate weed pests. They have gained a high degree of commercial success because it has been shown that such control can increase crop yield and reduce harvesting costs.

Herbicidal effectiveness is dependent upon several variables. One of these is the time or growth related method of application. The most popular methods of application include: pre-plant incorporation into the soil; pre-emergence surface treatment of seeded soil; and post-emergence treatment of the plant and soil.

The most important determinant of herbicidal effectiveness is the susceptibility of the beneficial crop and selectivity toward weeds. Certain herbicidal compounds are phytotoxic to some weed species but not to others.

A manufacturer of a herbicide generally recommends a range of rates and concentrations calculated to maximize weed control. The range of rates usually varies from approximately 0.1 to approximately 50 pounds per acre (lb/A) [0.112 to 58 kilograms per hectare (k/ha)], usually from 0.1 to 25 lb/A (0.112 to 26 k/ha). The actual amount used depends upon several considerations, including, crop tolerance, particular weed susceptibility and overall cost limitations.

Some herbicides display exclusive selectivity toward weed species. Many are toxic to both weeds and the intended crop beneficiary. Therefore, a particular herbicide may proscribe its injurious effect on the cultivated crop even though it may otherwise provide excellent control of weeds found in the crop field.

To preserve the beneficial aspects of herbicide use and to mitigate crop damage, many herbicidal antidotes have been prepared. These antidotes reduce or eliminate damage to the crop without substantially impairing the beneficial effect of the herbicide. For example, see U.S. Pat. Nos. 4,021,224 and 4,021,229 and Belgian Pat. No. 846,894.

Although several explanatory theories have been advanced, the precise mechanism by which an antidote reduces herbicidal crop injury while retaining weed injury has not been conclusively established. An antidote compound may in fact be a remedy, interferent, protectant or antagonist. As used herein, "antidote" describes, i.e., the continued effect of establishing herbicidal selectivity of herbicidal phytotoxicity to weed species and reduced or non-phytotoxicity to cultivated crop species.

As an alternative mode of action, the compounds of this invention may interfere with the normal herbicidal action of the thiolcarbamate-type herbicides to render them selective in their action. Whichever mode of action is present, the corresponding beneficial and desirable effect is the continued herbicidal effect of the thiolcarbamate with the accompanying decreased herbicidal effect on desired crop species. This advantage and utility will become more apparent hereinafter.

Therefore, the terms "herbicide antidotes" or "antidotal amount" is meant to describe that effect or the amount which produces the effect which tends to counteract the normal injurious herbicidal response that the herbicide might otherwise produce. Whether it is to be termed a remedy, interferent, protectant, or the like, will depend upon the exact mode of action. The mode of action is varied, but the effect, which is desirable, is the result of the method of treating the soil in which a crop is planted.

Thiolcarbamate herbicides are particularly effective in the control of grassy type weeds which interfere with the cultivation of a wide variety of crops, e.g., barley, corn, lentils, peanuts, peas, potatoes, soybeans, spinach, tobacco and tomatoes. Frequently, the beneficial use of the thiolcarbamate can be enhanced by the addition of an antidote compound.

DESCRIPTION OF THE INVENTION

It has been discovered that certain acylphenyl-thiourea compounds are effective antidotes for the protection of crops from thiolcarbamate herbicidal injury. Such compounds have the formula

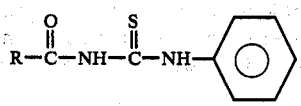

in which R is alkyl having 1–4 carbon atoms, preferably methyl.

This invention is a herbicidal composition comprised of (a) a non-phytotoxic antidotally effective amount of an acyl-phenyl-thiourea compound of the formula

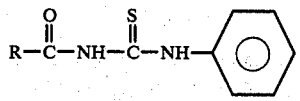

in which R is alkyl having 1–4 carbon atoms, preferably methyl; and (b) a herbicidally effective amount of a thiolcarbamate of the formula

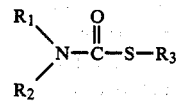

in which
  $R_1$ is selected from the group consisting of alkyl having 1–6 carbon atoms and alkenyl having 2–6 carbon atoms;
  $R_2$ is selected from the group consisting of alkyl having 1–6 carbon atoms, alkenyl having 2–6 carbon atoms, cyclohexyl and phenyl; or
  $R_1$ and $R_2$ together form an alkylene group having 5–10 carbon atoms; and
  $R_3$ is selected from the group consisting of alkyl having 1–6 carbon atoms, haloalkyl having 1–4 carbon atoms, cycloalkyl having 5–10 carbon atoms, phenyl, substituted phenyl, wherein the substituents are alkyl having 1-4 carbon atoms, haloalkyl having 1-4 carbon atoms, and halo, benzyl, and substituted benzyl, wherein the substituents are alkyl having 1-4 carbon atoms, haloalkyl having 1-4 carbon atoms, and halo.

The terms "alkyl" and "alkenyl" as used herein are intended to include both straight- and branched-chain groups. The term "halo" is intended to include mono- and polyhalo groups and includes, chloro, bromo, iodo, fluoro and mixtures thereof. All carbon atom ranges are intended to be inclusive of both upper and lower limits. Exemplary of "alkyl" are methyl, ethyl, n-propyl, isopropyl, n-butyl, isobutyl, tertiarybutyl, pentyl, hexyl, and the like. Exemplary of "alkenyl" are such groups as vinyl, proenyl, butenyl, pentyl, hexenyl and the like. Exemplary of cycloalkyl are cyclopentyl, cyclohexyl, 2,2 dimethyl cyclohexyl, cycloheptyl and the like.

By way of exemplification, the active thiolcarbamate herbicides employed in the invention may include the following: EPTC, S-ethyl diisobutyl thiocarbamate, S-propyl dipropyl thiocarbamate, S-2,3,3-trichloroallyl-diisopropyl thiocarbamate, S-ethyl cyclohexyl ethyl thiocarbamate, S-ethyl hexahydro-1H-azepine-1-carbothioate, S-4-chlorobenzyl diethyl thiocarbamate, and combinations thereof.

This invention also includes the method of protecting crops from herbicidal injury which comprises applying to the locus where protection is desired an antidotally effective amount of an acyl-phenyl-thiourea compound of the formula

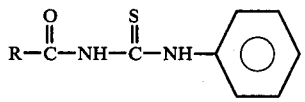

in which R is alkyl having 1-4 carbon atoms, preferably methyl.

Preparation

The thiocarbamates of the present compositions can be prepared by the procedures described in U.S. Pat. Nos. 2,913,327, 2,983,747, 3,133,947, 3,185,720 and 3,198,786.

1-Acetyl-3-phenyl-thiourea, which is representative of the genus of this invention, is commercially available.

Testing

Stock solutions of the herbicides are generally prepared by diluting the requisite amount of the formulated herbicide in water. The solution compositions and application rates are summarized in Table I.

TABLE I

| | Herbicide Stock Solutions | | | |
| | Composition | | Application | |
| Herbicide Name | Herbicide (mg) | Water (ml) | ml/flat | lb/acre |
| --- | --- | --- | --- | --- |
| VERNAM ® 6E S-propyl-N,N-dipropylthiocarbamate | 550 2730 | 400 400 | 4 4 | 1.00 6.00 |
| EPTAM ® 6E S-ethyl N,N-dipropylthiocarbamate | 3200 | 500 | 5 | 6.00 |

Stock solutions of the antidotes were prepared by diluting the requisite amount of the compound in acetone. The compositions and application rates appear in Table II.

TABLE II

| Antidote Stock Solutions | | | | |
| Compostion | | Application | | |
| Antidote (mg) | Acetone (ml) | ml/flat | ~lb/acre | Method* |
| --- | --- | --- | --- | --- |
| 1-acetyl-3-phenyl-thiourea | | | | |
| 95 | 15 | 1.5 | 5.00 | IF |
| Stock A: | | | | |
| 20 | 50 | 5.0 | 0.50 | PPI |
| Stock B: | | | | |
| 5 ml of A | 45 | 5.0 | 0.05 | PPI |
| Stock C: | | | | |
| 10 ml of B | 30 | 5.0 | 1/80 | PPI |

*IF = In Furrow
PPI = Pre-Plant Incorporation of Antidote and Herbicide.

All of the soil used in the tests described herein was loamy sand soil treated with 50 parts per million (ppm) each of a commercially available fungicide, N-[trichloromethyl)-thio]-4-cyclohexene-1,2-dicarboximide, and 18-18-18 fertilizer, which contains 18% by weight equivalent each of nitrogen, phosphorus pentoxide, and potassium oxide.

The herbicides were applied to the soil by pre-plant incorporation (PPI) into the soil prior to seeding. The antidotes were applied either in-furrow (IF) or by pre-plant incorporation.

For (IF) antidote applications, planting flats were filled with soil treated by the (PPI) of the herbicide. A one pint sample of soil removed from each flat was retained to cover the seeds after treatment. After leveling and furrowing the soil, seeds of the crop or weed species were planted ½ inch deep. Each flat was divided into half by a wooden barrier. A stock solution of the antidote was atomized directly onto the exposed seeds and soil in the open furrows on one side of the barrier. The seeds in the entire flat were then covered with the previously removed soil. The antidotally untreated sections of flats were compared for observed differences which would indicate lateral movement of the antidote through the soil.

After planting, all flats were placed on greenhouse benches where temperature was maintained between 70° and 90° F. (21.1° to 32.2° C.). The flats were watered by sprinkling as needed to assure good plant growth.

Control flats contained crops treated with herbicides only at the various rates.

Injury ratings were taken four weeks after application of the antidote. The effectiveness of the antidote was determined by visual comparison of injuries to crops and weeds in the control and test flats to those in untreated flats.

The treated crops initially screened for diminution of herbicidal injury were milo, wheat, cotton, rice, barley, corn and soybeans. The herbicide-antidote compositions were tested for control of watergrass (*Echinochloa crusgalli*), and foxtail (*Setaria viridis*).

The antidote compound, 1-acetyl-3-phenyl-thiourea, when applied in-furrow at the rate of 5 lb/A to soil treated with the representative thiolcarbamate herbicide, VERNAM ® (S-propyl-N,N-dipropylthiolcarbamate), at the rate of 6 lb/A completely protected corn (Zea Maize) from injury. The untreated flat with VERNAM ® alone displayed 25 percent injury to the corn. When treated with the antidote compound, no injury (0 percent) occurred.

TABLE III

Herbicidal Effectiveness

Antidote: 1-acetyl-3-phenyl-thiourea

| Rate | Method | Herbicide Name | Rate | Watergrass U | T | Foxtail U | T |
|---|---|---|---|---|---|---|---|
| 0.50 | PPI | EPTAM | 6.00 | 100 | — | 100 | — |
| 0.05 | PPI | EPTAM | 6.00 | 100 | — | 100 | — |
| 1/80 | PPI | EPTAM | 6.00 | 100 | — | 100 | — |

Formulations

The object of the formulation is to apply the compositions to the locus where control is desired by a convenient method. The "locus" may include soil, seeds, seedlings and vegetation.

The amount of antidote compound which comprises part of a herbicidal composition will generally range from approximately 0.001 to 30 parts by weight per weight of the herbicidal compound.

Formulations will generally contain several additives. Among these are inert ingredients, diluent carriers, organic solvents, water, oil and water, water in oil emulsions, carriers of dusts and granules, and surface active wetting, dispersing and emulsifying agents. Fertilizers, e.g., ammonium nitrate, urea and superphosphate, may also be included. Aids to rooting and growth, e.g., compost, manure, humus, sand, etc., may likewise be included. The formulations are commonly dusts, wettable powders, granules, solutions or emulsifiable concentrates.

Dusts are free-flowing powder compositions containing the herbicidal compound impregnated on a particulate carrier. The particle size of the carriers is usually in the approximate range of 30 to 50 microns. Examples of suitable carriers are talc, bentonite, diatomaceous earth and pyrophyllite. Anti-caking and anti-static agents can be added, if desired. The composition generally contains up to 50% of active ingredient. Dusts, like liquid compositions, can be applied by spraying from boom and hand sprayers or airplanes.

Wettable powders are finely divided compositions comprising a particulate carrier impregnated with the herbicidal compound and additionally containing one or more surface active agents. The surface active agent promotes rapid dispersion of the powder in aqueous medium to form stable, sprayable suspensions. A wide variety of surface active agents can be used, for example, long chain fatty alcohols and alkali metal salts of the sulfated fatty alochols; salts of sulfonic acid; esters of long chain fatty acids; and polyhydric alcohols; in which the alcohol groups are free, omega-substituted polyethylene glycols of relatively long chain length. A list of surface active agents suitable for use in agriculture formulations can be found in Wade Van Valkenburg, *Pesticide Formulations* (Marcel Dekker, Inc., N.Y., 1973) at pages 79–84.

Granules comprise the herbicidal composition impregnated on a particulate inert carrier having a particle size of about 1 to 2 millimeters (mm) in diameter. The granules can be made by spraying a solution of the active ingredient in a volatile solvent onto the granular carrier. Suitable carriers in preparation of granules include clay, vermiculite, sawdust, granular carbon, etc.

The herbicidal compositions can also be applied to the soil in the form of a solution in a suitable solvent. Solvents frequently used in herbicidal formulations include kerosene, fuel oil, xylene, petroleum fractions with boiling ranges above xylene, and aromatic petroleum fractions rich in methylated naphthalenes.

Emulsifiable concentrates consist of an oil solution of the herbicide along with an emulsifying agent. Prior to use, the concentrate is diluted with water to form a suspended emulsion of oil droplets. The emulsifiers used are usually a mixture of anionic and nonionic surfactants. Other additives such as spreading agents and stickers can be included in the emulsifiable concentrate.

The compounds and compositions of this invention can also be applied by addition to irrigation water supplied to the field to be treated. This method of application permits the penetration of the compositions into the soil as the water is absorbed therein.

It is not necessary that the compounds and compositions be admixed with the soil particles. After application by the above discussed methods, they may be distributed below the surface to a depth of at least one-half inch by conventional means such as discing, dragging or mixing.

I claim:

1. A herbicidal composition comprising
   (a) a non-phytotoxic antidotally effective amount of a compound of the formula

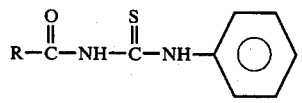

in which R is alkyl having 1–4 carbon atoms; and
   (b) a herbicidally effective amount of a thiolcarbamate herbicide of the formula

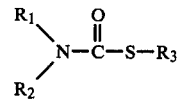

in which
   $R_1$ is selected from the group consisting of alkyl having 1–6 carbon atoms and alkenyl having 2–6 carbon atoms;
   $R_2$ is selected from the group consisting of alkyl having 1–6 carbon atoms, alkenyl having 2–6 carbon atoms, cyclohexyl and phenyl; or
   $R_1$ and $R_2$ together form an alkylene group having 5–10 carbon atoms; and
   $R_3$ is selected from the group consisting of alkyl having 1–6 carbon atoms, haloalkyl having 1–6 carbon atoms, cycloalkyl having 5–10 carbon atoms, phenyl, substituted phenyl, wherein the substituents are alkyl having 1–4 carbon atoms, haloalkyl having 1–4 carbon atoms, and halo, benzyl and substituted benzyl, wherein the substituents are alkyl having 1–4 carbon atoms, haloalkyl having 1–4 carbon atoms, and halo; wherein said antidote compound is present in an amount ranging between about 0.001 to 30 parts by weight for each part by weight of the thiolcarbamate herbicidal compound.

2. A composition according to claim 1 in which R is methyl, and $R_1$, $R_2$ and $R_3$ are each propyl.

3. A method of controlling undesirable vegetation while reducing herbicidal injury to crops due to thiolcarbamate herbicides which comprises adding to the soil a non-phytotoxic antidotally effective amount of a compound of the formula

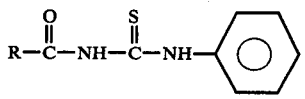

in which R is alkyl having 1–4 carbon atoms.

4. A method of controlling undesirable vegetation while reducing herbicidal injury to crops due to thiolcarbamate herbicides which comprises adding to the soil a non-phytotoxic antidotally effective amount of a compound of the formula

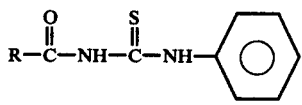

in which

R is alkyl having 1–4 carbon atoms; and a herbicidally effective amount of a thiolcarbamate of the formula $$\begin{array}{c} R_1 \\ \phantom{R_1}\diagdown \\ \phantom{R_1}N-\overset{\overset{\displaystyle O}{\|}}{C}-S-R_3 \\ \phantom{R_1}\diagup \\ R_2 \end{array}$$

in which
  $R_1$ is selected from the group consisting of alkyl having 1–6 carbon atoms and alkenyl having 2–6 carbon atoms;
  $R_2$ is selected from the group consisting of alkyl having 1–6 carbon atoms, alkenyl having 2–6 carbon atoms, cyclohexyl and phenyl; or
  $R_1$ and $R_2$ together form an alkylene group having 5–10 carbon atoms; and
  $R_3$ is selected from the group consisting of alkyl having 1–6 carbon atoms, haloalkyl having 1–6 carbon atoms, cycloalkyl having 5–10 carbon atoms, phenyl, substituted phenyl, wherein the substituents are alkyl having 1–4 carbon atoms, haloalkyl having 1–4 carbon atoms, and halo, benzyl and substituted benzyl, wherein the substituents are alkyl having 1–4 carbon atoms, haloalkyl having 1–4 carbon atoms, and halo; wherein said antidote compound is present in an amount ranging between about 0.001 to 30 parts by weight for each part by weight of the thiolcarbamate herbicidal compound.

* * * * *